United States Patent
Nir et al.

(10) Patent No.: US 11,832,790 B2
(45) Date of Patent: *Dec. 5, 2023

(54) METHOD OF ALERTING A USER TO OFF-SCREEN EVENTS DURING SURGERY

(71) Applicant: Asensus Surgical Europe S.a.r.l, Lugano (CH)

(72) Inventors: Tal Nir, Haifa (IL); Yehuda Pfeffer, Moshav Dvorah (IL)

(73) Assignee: Asensus Surgical Europe S.a.r.l, Lugano (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/119,259

(22) Filed: Mar. 8, 2023

(65) Prior Publication Data

US 2023/0218151 A1    Jul. 13, 2023

Related U.S. Application Data

(63) Continuation of application No. 17/190,310, filed on Mar. 2, 2021, now Pat. No. 11,730,347, which is a continuation of application No. 15/232,836, filed on Aug. 10, 2016, now Pat. No. 10,932,657, which is a continuation-in-part of application No. PCT/IL2015/050345, filed on Mar. 31, 2015.

(60) Provisional application No. 62/203,936, filed on Aug. 12, 2015.

(51) Int. Cl.
| | |
|---|---|
| *A61B 1/045* | (2006.01) |
| *A61B 90/00* | (2016.01) |
| *H04N 23/50* | (2023.01) |
| *A61B 1/00* | (2006.01) |
| *G02B 13/06* | (2006.01) |
| *G02B 23/24* | (2006.01) |
| *H04N 23/58* | (2023.01) |
| *H04N 23/60* | (2023.01) |

(52) U.S. Cl.
CPC ........ *A61B 1/00183* (2013.01); *A61B 1/0004* (2022.02); *A61B 1/0005* (2013.01); *A61B 1/00009* (2013.01); *A61B 1/00045* (2013.01); *A61B 1/00188* (2013.01); *A61B 1/045* (2013.01); *G02B 13/06* (2013.01); *G02B 23/243* (2013.01); *H04N 23/58* (2023.01); *H04N 23/60* (2023.01); *A61B 90/37* (2016.02); *H04N 23/555* (2023.01)

(58) Field of Classification Search
None
See application file for complete search history.

(56) References Cited

U.S. PATENT DOCUMENTS

| | | | | |
|---|---|---|---|---|
| 5,185,667 A | * | 2/1993 | Zimmermann | G06T 3/0062 348/E7.087 |
| 5,313,306 A | * | 5/1994 | Kuban | G06T 3/0018 348/240.99 |
| 5,547,455 A | * | 8/1996 | McKenna | A61B 1/0005 600/113 |
| 5,800,341 A | * | 9/1998 | McKenna | H04N 23/54 600/173 |

(Continued)

*Primary Examiner* — John P Leubecker

(57) ABSTRACT

An image of a field of view is captured by the endoscope and a portion of the image is displayed on a display. A popup image is generated and displayed upon image analysis identification of an occurrence of bleeding or motion of edges of an incision that is within the field of view, but outside the portion of the field of view displayed on the display.

14 Claims, 10 Drawing Sheets

(56) References Cited

U.S. PATENT DOCUMENTS

| Patent/Publication No. | Date | Name | Classification |
|---|---|---|---|
| 5,836,869 A * | 11/1998 | Kudo | A61B 1/00009 600/173 |
| 6,036,637 A * | 3/2000 | Kudo | A61B 1/00042 600/173 |
| 6,243,131 B1 * | 6/2001 | Martin | G08B 13/19658 348/206 |
| 6,255,746 B1 * | 7/2001 | Takahashi | G05B 19/042 307/112 |
| 6,656,110 B1 * | 12/2003 | Irion | A61B 1/00045 600/117 |
| 6,930,705 B2 * | 8/2005 | Tanaka | A61B 1/0005 348/E7.086 |
| 7,136,098 B1 * | 11/2006 | Burnett | H04N 23/73 348/E5.037 |
| 7,684,851 B2 * | 3/2010 | Miyake | A61B 1/3132 600/173 |
| 8,758,234 B2 * | 6/2014 | Hale | A61B 1/00179 359/206.1 |
| 2003/0135092 A1 * | 7/2003 | Cline | A61B 5/0084 600/178 |
| 2008/0004603 A1 * | 1/2008 | Larkin | A61B 34/10 606/1 |
| 2008/0108873 A1 * | 5/2008 | Gattani | A61B 1/045 382/128 |
| 2008/0231692 A1 * | 9/2008 | Higuchi | H04N 5/2628 348/E7.085 |
| 2009/0245600 A1 * | 10/2009 | Hoffman | A61B 34/30 348/240.99 |
| 2009/0248036 A1 * | 10/2009 | Hoffman | A61B 34/32 606/130 |
| 2010/0134264 A1 * | 6/2010 | Nagamine | B60Q 9/005 348/113 |
| 2010/0217075 A1 * | 8/2010 | Shigeta | A61B 1/00045 600/104 |
| 2011/0007129 A1 * | 1/2011 | Martin | H04N 23/58 348/36 |
| 2014/0031659 A1 * | 1/2014 | Zhao | G06T 7/269 600/371 |
| 2014/0046131 A1 * | 2/2014 | Morita | A61B 1/00177 600/109 |
| 2014/0118551 A1 * | 5/2014 | Ikeda | G06V 20/58 348/148 |
| 2014/0135792 A1 * | 5/2014 | Larkin | A61B 34/37 606/130 |
| 2014/0194722 A1 * | 7/2014 | Lee | A61B 8/466 600/407 |
| 2014/0323801 A1 * | 10/2014 | Konno | A61B 1/00193 600/103 |
| 2014/0375683 A1 * | 12/2014 | Salter | G06F 3/011 345/633 |
| 2014/0378763 A1 * | 12/2014 | Atarot | A61B 34/35 600/109 |
| 2015/0078615 A1 * | 3/2015 | Staples, II | G06T 7/50 382/103 |
| 2015/0213602 A1 * | 7/2015 | Verstraeten | G06F 3/04842 715/781 |
| 2015/0238071 A1 * | 8/2015 | Hua | A61B 1/3132 600/109 |
| 2016/0012604 A1 * | 1/2016 | Firouzian | G16H 50/30 382/128 |
| 2016/0231411 A1 * | 8/2016 | Kumar | G01S 3/7864 |
| 2016/0275709 A1 * | 9/2016 | Gotman | G06T 11/003 |
| 2016/0379363 A1 * | 12/2016 | Kitamura | A61B 1/0005 600/371 |
| 2017/0027650 A1 * | 2/2017 | Merck | A61B 1/00188 |
| 2017/0035278 A1 * | 2/2017 | Ojima | A61B 1/051 |
| 2017/0303869 A1 * | 10/2017 | Goshen | A61B 6/5229 |
| 2017/0305016 A1 * | 10/2017 | Larkin | A61B 90/37 |
| 2017/0367566 A1 * | 12/2017 | Kikuchi | H04N 13/239 |
| 2018/0035895 A1 * | 2/2018 | Herzlinger | A61B 1/000095 |
| 2018/0296280 A1 * | 10/2018 | Kurihara | A61B 34/30 |

* cited by examiner

METHOD OF ALERTING A USER TO OFF-SCREEN EVENTS DURING SURGERY

CROSS-REFERENCE TO RELATED APPLICATIONS

This application is a Continuation of U.S. application Ser. No. 17/190,310, filed Mar. 2, 2021, now U.S. Pat. No. 11,730,347, which is a Continuation of U.S. application Ser. No. 15/232,836, filed Aug. 10, 2016, now U.S. Pat. No. 10,932,547, which is a Continuation-in-Part of International Application No. PCT/IL2015/050345, filed Mar. 31, 2015, claiming priority from U.S. Provisional Patent Application No. 61/973,906, filed Apr. 2, 2014, and Continuation-in-Part of U.S. Provisional Patent Application No. 62/203,936, filed Aug. 12, 2015, the disclosures of which are hereby incorporated by reference in their entirety.

FIELD OF THE INVENTION

The present invention generally pertains to a system and method for providing an endoscopic image, where the field of view of the image can be maneuvered digitally.

BACKGROUND OF THE INVENTION

Laparoscopic surgery is becoming increasingly popular with patients because the scars are smaller and their period of recovery is shorter. Laparoscopic surgery requires special training of the surgeon or gynecologist and the theatre nursing staff. The equipment is often expensive and is not available in all hospitals. During laparoscopic surgery it is often required to shift the spatial placement of the endoscope in order to present the surgeon with the optimal view. Conventional laparoscopic surgery makes use of either human assistants that manually shift the instrumentation or alternatively robotic automated assistants (such as JP patent No. 06063003).

In laparoscopic surgery, the surgeon performs the operation through small holes using long instruments and observing the internal anatomy with an endoscope camera. The surgeon's performance is largely dependent on the camera position relative to the instruments and on a stable image shown at the monitor. In general, the surgeon needs a close-up view of the area in which he wants to work, however, there are times when an overview of a large portion of the working area, such as an overall view of the interior of the abdomen, is desirable. U.S. Pat. No. 6,387,044 discloses a laparoscope apparatus for use in laparoscopic surgery or the like comprises a cannula with an inner hollow having therein a light guide for introducing light to its tip end for illuminating the object to be observed, and an endoscope which is capable of being pulled into and out from the inner hollow of the cannula. The cannula is airtightly sealed with a transparent member at its tip end, while the endoscope has therein an image pickup with a wide-angle lens, and the image pick-up is housed in the cannula close to the transparent member.

However, in U.S. Pat. No. 6,387,044, no means of adjusting magnification of the image is disclosed.

Korean Patent Application KR2009/012326 discloses a laparoscope and an image processing system using the same to efficiently perform a laparoscope operation by outputting an image of the inside of the abdominal cavity. The laparoscope includes a wide angle lens, an optical fiber, an inserting part, and an optical interface part. The wide angle lens is arranged at one end of the laparoscope, and is a fisheye lens. The focal distance of the wide angle lens is controllable. The optical fiber delivers incident light from the wide angle lens to the camera part, and is received in an inner space of the inserting part. The inserting part is inserted inside the abdominal cavity. The optical interface part delivers the light delivered from the optical fiber to the camera part. The camera part is a two dimensional camera or a three dimensional camera.

However, Korean Patent Application KR2009/012326 requires camera wide angle lens of adjustable focal length.

U.S. Patent Application US2011069160 discloses an imaging system and method of application, including lens designs tailored to be used with particular transformation algorithms, electronic hardware and algorithms for image transformations. Exemplary application of the system including automotive, photographic and medical endoscopic are also described. The system enables improved image view and allows customization of views by the end user even after installation of the image system hardware. In U.S. Patent Application US2011069160, mathematical algorithms are used to alter the image, so that a continuously varying distortion of the image is possible, so that desired portions of the image are magnified, but the whole of the image remains within the field of view.

However, US Patent Application US2011069160 discloses a system wherein the image is distorted, with the distortion changing continuously across the image, so that portions of the image are magnified while the entirety of the field of view is displayed.

Chinese Utility Model CN203042209 discloses a laparoscopic puncture device with an intra-cavity full-view auxiliary lens, which relates to a surgical instrument device, in particular to the laparoscopic puncture device with the intra-cavity full-view auxiliary lens for abdominal cavity minimally-invasive surgery. A main lens of a laparoscope enters into the abdominal cavity through a cannular puncture device, the puncture device is provided with an auxiliary lens which can be used for observing intra-cavity full view, and the auxiliary lens is a wide-angle lens and cold light source combination body; the auxiliary lens is arranged at the middle part of the puncture device entering into the abdominal cavity, and the auxiliary lens is positioned at the highest position of the abdominal cavity after the abdominal cavity is subjected to air inflation; the outer ring of the puncture device is provided with a groove, the wide-angle lens and cold light source combination body of the auxiliary lens is embedded in the groove and is combined into a whole with the puncture device; and the wide angle of a wide-angle lens of the auxiliary lens is larger than or equal to 270 degrees, and the resolution ratio of the wide-angle lens of the auxiliary lens is 1-3 million pixels. By adding a cold light source and the wide-angle lens, the full-view visible function is added on the basis of the original function of the puncture device, 80 percent of the abdominal cavity can be within a visible range, motion of all instruments is within the visible range, the surgical blind area of a surgeon can be removed, and the surgery can be safer.

However, Chinese Utility Model CN203042209 requires use of at least two lenses.

It is therefore a long felt need to provide an endoscopic image, where the field of view of the image can be maneuvered digitally.

SUMMARY OF THE INVENTION

It is an object of the present invention to disclose a system for providing an endoscopic image, where the image can be maneuvered digitally.

It is another object of the present invention to disclose a system for altering the field of view of an endoscope image, comprising:

a. at least one endoscope having at least one wide-angle lens in said endoscope's distal end;
b. at least one camera located in said endoscope's proximal end, configured to image a field of view of said endoscope image by means of said wide-angle lens; and
c. at least one computer program which, when executed by data processing apparatus, is configured to select at least a portion of said field of view;

wherein said portion of said field of view is selectable without necessarily physically maneuvering said endoscope or said wide-angle lens such that substantially all of said maneuvering of said field of view is provided via said executing computer program.

It is another object of the present invention to disclose the system as described hereinabove, wherein said field of view can encompass a substantial portion of a surgical field.

It is another object of the present invention to disclose the system as described hereinabove, further comprising at least one display in communication with said camera, said display configured to show at least a portion of said selected portion of said field of view.

It is another object of the present invention to disclose the system as described hereinabove, wherein said at least one computer program is further configured, when executed by data processing apparatus, to identify from at least one said image of said field of view, the occurrence of at least one predetermined item of interest.

It is another object of the present invention to disclose the system as described hereinabove, wherein said item of interest is selected from a group consisting of: an article entering the field of view of the lens, an article moving, a likely collision between two articles, the occurrence of bleeding, the edges of an incision moving, activation or deactivation of a tool, articulation of a tool, and any combination thereof.

It is another object of the present invention to disclose the system as described hereinabove, wherein, if at least one said item of interest is identifiable, a warning is activatable.

It is another object of the present invention to disclose the system as described hereinabove, wherein said warning is selected from a group consisting of a visual warning, an aural warning and any combination thereof.

It is another object of the present invention to disclose the system as described hereinabove, wherein said aural warning is selected from a group consisting of a predetermined voice message or a predetermined sound.

It is another object of the present invention to disclose the system as described hereinabove, wherein said visual warning is selected from a group consisting of a flashing light, a steady light, a region on said display changing in quality, and any combination thereof.

It is another object of the present invention to disclose the system as described hereinabove, wherein said change in quality is selected from a group consisting of: a changing color, a changing brightness, a pop-up appearing, an icon ungreying, a symbol ungreying, and any combination thereof.

It is another object of the present invention to disclose the system as described hereinabove, wherein said display comprises at least one predetermined location, said predetermined location configured to display, for a predetermined time, at least one said warning.

It is another object of the present invention to disclose the system as described hereinabove, wherein said item of interest is displayable as a member of a group consisting of: a display including said item of interest substantially entirely replaces a previous display, a display field of view which includes said item of interest appears as a popup, a display including said item of interest replaces a portion of a previous display field of view and any combination thereof.

It is another object of the present invention to disclose the system as described hereinabove, wherein digital zoom is selected from a group consisting of: straight enlargement, interpolating zoom and any combination thereof.

It is another object of the present invention to disclose the system as described hereinabove, wherein, for at least two camera pixels, for cases where at least a portion of each pixel maps onto at least a portion of a display pixel, said straight enlargement is selected from a group consisting of averaging between said at least two camera pixels, interpolating between said at least two camera pixels and any combination thereof.

It is another object of the present invention to disclose the system as described hereinabove, wherein, in conjunction with said identification of said occurrence of said at least one predetermined item of interest, a field of view encompassing said item of interest can be provided.

It is another object of the present invention to disclose the system as described hereinabove, wherein at least a portion of a current field of view is replaceable by said field of view encompassing said item of interest.

It is another object of the present invention to disclose the system as described hereinabove, wherein said replacement of said at least a portion of said current field of view is commandable via at least one predetermined location on said display.

It is another object of the present invention to disclose the system as described hereinabove, wherein said camera is a high-resolution camera.

It is another object of the present invention to disclose the system as described hereinabove, additionally comprising a database.

It is another object of the present invention to disclose the system as described hereinabove, wherein at least one said portion of said field of view is storable in said database.

It is another object of the present invention to disclose the system as described hereinabove, wherein said at least one computer program, when executed, can alter the apparent size of said portion of said field of view.

It is another object of the present invention to disclose the system as described hereinabove, wherein said at least one computer program, when executed, can show said portion of said field of view on said display.

It is another object of the present invention to disclose the system as described hereinabove, wherein said digital maneuvering is either continuous or discrete.

It is another object of the present invention to disclose the system as described hereinabove, wherein said image of said at least a portion of said field of view is substantially undistorted.

It is another object of the present invention to disclose the system as described hereinabove, wherein said at least one computer program, when executed by said data processing apparatus, is additionally configured to perform said digital maneuvering automatically.

It is another object of the present invention to disclose the system as described hereinabove, wherein said automatic digital maneuvering is performed in order to achieve a predetermined goal, said goal selected from a group consisting of: maintaining a predetermined object at the center of said portion of said field of view, maintaining a predetermined object at a predetermined apparent size; maintaining a predetermined horizon, and any combination thereof.

It is another object of the present invention to disclose the system as described hereinabove, wherein said system additionally comprises a maneuvering mechanism for physically maneuvering said endoscope.

It is another object of the present invention to disclose the system as described hereinabove, wherein said at least one computer program, when executed by said data processing apparatus, is additionally configured to physically maneuver said endoscope by means of said maneuvering mechanism.

It is another object of the present invention to disclose the system as described hereinabove, wherein said at least one computer program, when executed by said data processing apparatus, is additionally configured to maneuver said portion of said field of view by means of a group consisting of said physical maneuvering, said digital maneuvering and any combination thereof.

It is another object of the present invention to disclose the system as described hereinabove, wherein said maneuvering of said field of view is commanded by means of a member of a group consisting of: moving an object, touching a prepared surface, typing on a keyboard, a gesture, a non-gesture body movement, generating a predetermined sound and any combination thereof.

It is another object of the present invention to disclose the system as described hereinabove, wherein said movable object is selected from a group consisting of: a joystick, a lever, a button, a slider and any combination thereof.

It is another object of the present invention to disclose the system as described hereinabove, wherein said prepared surface is selected from a group consisting of: a touch-sensitive pad displaying commands, a display comprising a touchscreen and any combination thereof.

It is another object of the present invention to disclose the system as described hereinabove, wherein selection of a center of said field of view is by means of touching said touchscreen.

It is another object of the present invention to disclose the system as described hereinabove, wherein selection of zoom is selected from a group consisting of: drawing the outline of a desired image area on said display, continuing to touch said touchscreen until zoom is complete and any combination thereof.

It is another object of the present invention to disclose the system as described hereinabove, wherein said gesture is selected from a group consisting of: a hand movement, an arm movement, a body movement, a head movement, an eye movement and any combination thereof.

It is another object of the present invention to disclose the system as described hereinabove, wherein said sound comprises at least one predetermined sound pattern.

It is another object of the present invention to disclose the system as described hereinabove, wherein said predetermined sound pattern is selected from a group consisting of a word, a sound of constant pitch, a sound of varying pitch, a sound of constant loudness, a sound of varying loudness and any combination thereof.

It is another object of the present invention to disclose the system as described hereinabove, wherein said at least one movement of said at least one moving element is an unwanted movement of said moving element.

It is another object of the present invention to disclose the system as described hereinabove, wherein said output procedure for movement of said surgical tool, upon detection of said at least one said unwanted movement of said moving element, is that, for said moving element being said surgical tool, said unwanted movement is removed from said movement of said surgical tool; or, for said moving element not being said surgical tool, movement of said surgical tool is unaffected by said detection of said at least one unwanted movement.

It is another object of the present invention to disclose the system as described hereinabove, wherein said unwanted movement is selected from a group consisting of: involuntary movement of a body part, saccadic movement of an eye, vestibulo-ocular movement of an eye, winking an eye, blinking an eye, tremor of a body part, a tic in a body part, myoclonus of a body part, dystonia, and any combination thereof.

It is another object of the present invention to disclose the system as described hereinabove, wherein said at least one camera generates a plurality of images.

It is another object of the present invention to disclose the system as described hereinabove, wherein said plurality of images is combinable to form a display selected from a group consisting of: a unitary two dimensional display; a unitary three dimensional display; a stereoscopic display and any combination thereof.

It is another object of the present invention to disclose the system as described hereinabove, additionally comprising at least one illumination controlling computer program configured, when executed, to control at least one aspect of illumination of said field of view.

It is another object of the present invention to disclose the system as described hereinabove, wherein said controllable aspect of said illumination is selected from a group consisting of: number of sources of said illumination, intensity of a source of said illumination, wavelength range of a source of said illumination, number of light beams from a source of said illumination, direction of at least one light beam from a source of said illumination, angular width of at least one light beam from a source of said illumination, diameter of at least one light beam from a source of said illumination and any combination thereof.

It is another object of the present invention to disclose the system as described hereinabove, wherein said wavelength range is selected from a group consisting of: at least a portion of an infrared wavelength range, at least a portion of a visible wavelength range, at least a portion of an ultraviolet wavelength range, at least a portion of an X-ray wavelength range and any combination thereof.

It is another object of the present invention to disclose the system as described hereinabove, wherein, for each said source of said illumination, intensity of said illumination is selected from a group consisting of stepwise variable or substantially continuously variable.

It is another object of the present invention to disclose the system as described hereinabove, wherein, for each said source of said illumination, at least a portion of said source of said illumination is held by at least one light holder.

It is another object of the present invention to disclose the system as described hereinabove, wherein at least one said light holder is an endoscope.

It is another object of the present invention to disclose the system as described hereinabove, wherein at least one said source of said illumination is directable via a wide-angle lens.

It is another object of the present invention to disclose a method for altering the field of view of an endoscope image, comprising steps of:

a. providing a system for altering the field of view of an endoscope image, comprising:
   i. at least one endoscope having at least one wide-angle lens in said endoscope's distal end;
   ii. at least one camera located in said endoscope's proximal end, configured to image a field of view of said endoscope image by means of said wide-angle lens; and
   iii. at least one computer program which, when executed by data processing apparatus, is configured to select at least a portion of said field of view;
b. imaging said field of view of said endoscope image; and
c. selecting said at least a portion of said field of view thereby selecting said portion of said field of view without necessary physically maneuvering said endoscope or said wide-angle lens such that substantially all of said maneuvering of said field of view is provided via said executing computer program.

It is another object of the present invention to disclose the method as described hereinabove additionally comprising step of encompassing a substantial portion of a surgical field in said field of view.

It is another object of the present invention to disclose the method as described hereinabove additionally comprising steps of providing at least one display in communication with said camera, and of showing at least a portion of said selected portion of said field of view on said display.

It is another object of the present invention to disclose the method as described hereinabove, additionally comprising step of configuring said at least one computer program, when executed by data processing apparatus, to identify from at least one said image of said field of view, the occurrence of at least one predetermined item of interest.

It is another object of the present invention to disclose the method as described hereinabove, additionally comprising step of selecting said item of interest from a group consisting of: an article entering the field of view of the lens, an article moving, a likely collision between two articles, the occurrence of bleeding, the edges of an incision moving, activation or deactivation of a tool, articulation of a tool, and any combination thereof.

It is another object of the present invention to disclose the method as described hereinabove, additionally comprising step of activating a warning if at least one said item of interest is identifiable.

It is another object of the present invention to disclose the method as described hereinabove, additionally comprising step of selecting said warning from a group consisting of a visual warning, an aural warning and any combination thereof.

It is another object of the present invention to disclose the method as described hereinabove, additionally comprising step of selecting said aural warning from a group consisting of a predetermined voice message or a predetermined sound.

It is another object of the present invention to disclose the method as described hereinabove, additionally comprising step of selecting said visual warning from a group consisting of a flashing light, a steady light, a region on said display changing in quality, and any combination thereof.

It is another object of the present invention to disclose the method as described hereinabove, additionally comprising step of selecting said change in quality from a group consisting of: a changing color, a changing brightness, a pop-up appearing, an icon ungreying, a symbol ungreying, and any combination thereof.

It is another object of the present invention to disclose the method as described hereinabove, additionally comprising steps of providing said display with at least one predetermined location, and of displaying at said predetermined location, for a predetermined time, at least one said warning.

It is another object of the present invention to disclose the method as described hereinabove, additionally comprising step of selecting said display of said item of interest from a group consisting of: a display including said item of interest substantially entirely replacing a previous display, a display field of view which includes said item of interest appearing as a popup, a display including said item of interest replacing a portion of a previous display field of view and any combination thereof.

It is another object of the present invention to disclose the method as described hereinabove, additionally comprising step of selecting digital zoom from a group consisting of: straight enlargement, interpolating zoom and any combination thereof.

It is another object of the present invention to disclose the method as described hereinabove, additionally comprising step of selecting said straight enlargement, for at least two camera pixels, for cases where at least a portion of each pixel maps onto at least a portion of a display pixel, from a group consisting of averaging between said at least two camera pixels, interpolating between said at least two camera pixels and any combination thereof.

It is another object of the present invention to disclose the method as described hereinabove, additionally comprising step of providing, in conjunction with said identification of said occurrence of said at least one predetermined item of interest, a field of view encompassing said item of interest.

It is another object of the present invention to disclose the method as described hereinabove, additionally comprising step of replacing at least a portion of a current field of view by said field of view encompassing said item of interest.

It is another object of the present invention to disclose the method as described hereinabove, additionally comprising step of commanding said replacement of said at least a portion of said current field of view via at least one predetermined location on said display.

It is another object of the present invention to disclose the method as described hereinabove, additionally comprising step of selecting said camera to be a high-resolution camera.

It is another object of the present invention to disclose the method as described hereinabove, additionally comprising step of providing a database.

It is another object of the present invention to disclose the method as described hereinabove, additionally comprising step of storing at least one portion of said field of view in said database.

It is another object of the present invention to disclose the method as described hereinabove, additionally comprising step of altering the apparent size of said portion of said field of view.

It is another object of the present invention to disclose the method as described hereinabove, additionally comprising step of showing said portion of said field of view on said display.

It is another object of the present invention to disclose the method as described hereinabove, additionally comprising step of performing said digital maneuvering either continuously or discretely.

It is another object of the present invention to disclose the method as described hereinabove, additionally comprising step of providing said image of said at least a portion of said field of view substantially undistorted.

It is another object of the present invention to disclose the method as described hereinabove, additionally comprising step of configuring said at least one computer program, when executed by said data processing apparatus, to perform said digital maneuvering automatically.

It is another object of the present invention to disclose the method as described hereinabove, additionally comprising step of performing said automatic digital maneuvering in order to achieve a predetermined goal, said goal selected from a group consisting of: maintaining a predetermined object at the center of said portion of said field of view, maintaining a predetermined object at a predetermined apparent size; maintaining a predetermined horizon, and any combination thereof.

It is another object of the present invention to disclose the method as described hereinabove, additionally comprising step of providing said system with a maneuvering mechanism for physically maneuvering said endoscope.

It is another object of the present invention to disclose the method as described hereinabove, additionally comprising step of configuring said at least one computer program, when executed by said data processing apparatus, to physically maneuver said endoscope by means of said maneuvering mechanism.

It is another object of the present invention to disclose the method as described hereinabove, additionally comprising step of configuring said at least one computer program, when executed by said data processing apparatus, to maneuver said portion of said field of view by means of a group consisting of said physical maneuvering, said digital maneuvering and any combination thereof.

It is another object of the present invention to disclose the method as described hereinabove, additionally comprising step of commanding said maneuvering of said field of view by means of a member of a group consisting of: moving an object, touching a prepared surface, typing on a keyboard, a gesture, a non-gesture body movement, generating a predetermined sound and any combination thereof.

It is another object of the present invention to disclose the method as described hereinabove, additionally comprising step of selecting said movable object from a group consisting of: a joystick, a lever, a button, a slider and any combination thereof.

It is another object of the present invention to disclose the method as described hereinabove, additionally comprising step of selecting said prepared surface from a group consisting of: a touch-sensitive pad displaying commands, a display comprising a touchscreen and any combination thereof.

It is another object of the present invention to disclose the method as described hereinabove, additionally comprising step of selecting a center of said field of view by means of touching said touchscreen.

It is another object of the present invention to disclose the method as described hereinabove, additionally comprising step of selecting said zoom by means of a member of a group consisting of: drawing an outline of a desired image area on said display, continuing to touch said touchscreen until zoom is complete and any combination thereof.

The digital maneuvering of the FOV can also be performed automatically by an algorithm in order to achieve a predefined goal such as (but not limited to) centering a certain object in the image, zooming in\out in order to maintain a certain object size, rotating the image in order to maintain a constant horizon.

The digital maneuvering of the FOV can be combined with physical maneuvering of the laparoscope\endoscope by means of controlling the laparoscope position and orientation. The combination can be used in order to achieve more flexibility in the viewed image, such as when the laparoscope is inserted deeper in order to view beyond an occluded organ, while the FOV is digitally maneuvered in order to tilt the viewing angle.

It is another object of the present invention to disclose the method as described hereinabove, additionally comprising step of selecting said gesture from a group consisting of: a hand movement, an arm movement, a body movement, a head movement, an eye movement and any combination thereof.

It is another object of the present invention to disclose the method as described hereinabove, additionally comprising step of selecting said sound to be a predetermined sound pattern.

It is another object of the present invention to disclose the method as described hereinabove, additionally comprising step of selecting said predetermined sound pattern from a group consisting of a word, a sound of constant pitch, a sound of varying pitch, a sound of constant loudness, a sound of varying loudness and any combination thereof.

It is another object of the present invention to disclose the method as described hereinabove, additionally comprising step of selecting said at least one movement of said at least one moving element to be an unwanted movement of said moving element.

It is another object of the present invention to disclose the method as described hereinabove, additionally comprising step of selecting said output procedure for movement of said surgical tool, upon detection of said at least one said unwanted movement of said moving element, to be that, for said moving element being said surgical tool, said unwanted movement is removed from said movement of said surgical tool; or, for said moving element not being said surgical tool, movement of said surgical tool is unaffected by said detection of said at least one unwanted movement.

It is another object of the present invention to disclose the method as described hereinabove, additionally comprising step of selecting said unwanted movement from a group consisting of: involuntary movement of a body part, saccadic movement of an eye, vestibulo-ocular movement of an eye, winking an eye, blinking an eye, tremor of a body part, a tic in a body part, myoclonus of a body part, dystonia, and any combination thereof.

It is another object of the present invention to disclose the method as described hereinabove, additionally comprising step of generating a plurality of images from said at least one camera.

It is another object of the present invention to disclose the method as described hereinabove, additionally comprising steps of combining said plurality of images to form a display and of selecting said display from a group consisting of: a unitary two dimensional display; a unitary three dimensional display; a stereoscopic display and any combination thereof.

It is another object of the present invention to disclose the method as described hereinabove, additionally comprising steps of providing at least one illumination controlling computer program and of controlling at least one aspect of illumination of said field of view via said illumination controlling computer program.

It is another object of the present invention to disclose the method as described hereinabove, additionally comprising step of selecting said controllable aspect of said illumination from a group consisting of: number of sources of said illumination, intensity of a source of said illumination, wavelength range of a source of said illumination, number of light beams from a source of said illumination, direction of at least one light beam from a source of said illumination, angular width of at least one light beam from a source of said illumination, diameter of at least one light beam from a source of said illumination and any combination thereof.

It is another object of the present invention to disclose the method as described hereinabove, additionally comprising step of selecting said wavelength range from a group consisting of: at least a portion of an infrared wavelength range, at least a portion of a visible wavelength range, at least a portion of an ultraviolet wavelength range, at least a portion of an X-ray wavelength range and any combination thereof.

It is another object of the present invention to disclose the method as described hereinabove, additionally comprising step of selecting, for each said source of said illumination, intensity of said illumination from a group consisting of stepwise variable or substantially continuously variable.

It is another object of the present invention to disclose the method as described hereinabove, additionally comprising step of, for each said source of said illumination, holding at least a portion of said source of said illumination in at least one light holder.

It is another object of the present invention to disclose the method as described hereinabove, additionally comprising step of selecting at least one said light holder to be an endoscope.

It is another object of the present invention to disclose the method as described hereinabove, additionally comprising step of directing at least one said source of said illumination via a wide-angle lens.

BRIEF DESCRIPTION OF THE FIGURES

In order to better understand the invention and its implementation in practice, a plurality of embodiments will now be described, by way of non-limiting example only, with reference to the accompanying drawings, wherein FIG. 1 schematically illustrates fields of view in the prior art.

DETAILED DESCRIPTION OF THE PREFERRED EMBODIMENTS

Figure 1:
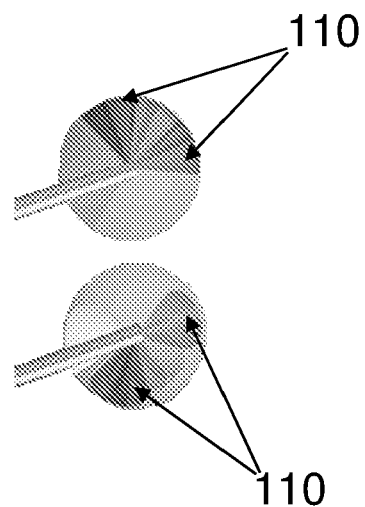

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for providing a laparoscopic or endoscopic image, which is digitally maneuverable.

The term 'camera' hereinafter refers to an image acquiring element. Examples of a camera include, but are not limited to, a CCD array and an electromagnetic system such as a TV camera.

The term 'endoscope tip' hereinafter refers to the end of the endoscope that is inside the patient. The camera is typically attached to the other side of the endoscope, outside of the patient's abdomen.

The term 'field of view' (FOV) hereinafter refers to the scene visible to the camera.

The term 'displayed view' hereinafter refers to the scene visible on a display.

The term 'digital maneuvering' hereinafter refers to maneuvering the field of view of an endoscope or laparoscope by using software to manipulate the image, such that both the center of the field of view and the extent of the field of view can be changed with or without physical movement of any portion of the endoscope or laparoscope, without physical movement of any portion of the camera and without movement of any lenses in the system.

Said digital maneuvering is provided by means of an image processing means that processes the image to provide change in the field of view. For example, if the image taken by the camera is an image of 270 degrees the processor can provide the user with an image of 30 degrees out of the 270 degrees. The user can then alter the field of view to another 30 degrees segment of said 270 degrees. All of this is done by image processing and not by physically maneuvering the endoscope.

The terms 'physical maneuvering' or 'optical maneuvering' hereinafter refer to maneuvering the field of view of an endoscope or laparoscope by physically moving at least one of (a) some part of the endoscope or laparoscope, (b) some portion of the camera, or (c) one or more lenses in the system.

The term 'wide-angle lens' hereinafter refers to any lens having a field of view of at least 30 degrees, preferably, at least 60 degrees, and, by extension, any endoscope containing such a lens. An example of an endoscope having a wide-angle lens is an endoscope capable of providing a 270 degree image.

Laparoscopic surgery, also called minimally invasive surgery (MIS), is a modern surgical technique in which operations in the abdomen are performed through small incisions (usually 0.5-1.5 cm) as compared to larger incisions needed in traditional surgical procedures. The key element in laparoscopic surgery is the use of an endoscope, which is a device configured for viewing the scene within the body, at the distal end of the endoscope. The at least one camera can be placed at the end of the endoscope, a rod lens system or fiber optic bundle can be used to direct the at least one image to the proximal end of the endoscope, and any combination thereof. Typically, also attached to the endoscope is at least one light source to illuminate the operative field, inserted through a 5 mm or 10 mm cannula or trocar to view the operative field.

The abdomen is usually injected with carbon dioxide gas to create a working and viewing space. The abdomen is essentially blown up like a balloon (insufflated), elevating the abdominal wall above the internal organs like a dome. Within this space, various medical procedures can be carried out.

For simplicity, in the embodiments hereinbelow, the system is described as producing a single image from a single camera. However, any of the embodiments described herein can comprise one or a plurality of cameras and, for any camera, one or a plurality of images can be produced.

In embodiments with a plurality of cameras, the images therefrom can be combined to form a unitary two dimensional display; the images therefrom can be combined to form a unitary three dimensional display; the images therefrom can be used to provide a stereoscopic display, simulating a three-dimensional display; and any combination thereof.

In some embodiments, at least one light source is controllable by the system. In preferred variants of these embodiments, the controllable features of the light include, but are not limited to, the intensity of the light source, the wavelength range of the light source, the direction of the beam for the light source, the angular width of the beam, the diameter of the beam and any combination thereof. Wavelength ranges can include, but are not limited to, at least a portion of an infrared wavelength range, at least a portion of the visible wavelength range, at least a portion of a UV wavelength range, at least a portion of an X-ray wavelength range and any combination thereof. For each source, light intensity can be stepwise variable (an on/off source has two steps) or substantially continuously variable (often described as infinitely variable). Light can enter the surgical field via the endoscope, or from a separate illuminator.

In preferred variants of embodiments with a plurality of cameras, all of the cameras are comprised in a single endoscope, thereby preventing unexpected differential movement between cameras due to mechanical drift or movement error and ensuring that there is proper registration of the images at all times.

In preferred variants of embodiments with a plurality of light sources, all of the light sources are comprised in a light source holder, thereby preventing unexpected differential movement between light sources due to mechanical drift or movement error and ensuring that the surgical field is properly illuminated at all times. In some embodiments, the endoscope comprises the light source holder. In some embodiments, the endoscope comprises both the light sources and the cameras, thereby obviating a possible source of error in illuminating regions viewed by at least one camera.

In some embodiments, at least one light source is directed into the surgical field via a wide-angle lens such that a significant portion of the surgical field, preferably substantially all of it, can be illuminated via the single wide-angle lens.

In some variants of embodiments where the light enters the surgical field via a wide-angle lens, at least one light source passes through only a portion of the lens. In such embodiments, the region of the surgical field illuminated by the light source will depend on the portion of the lens through which the light passes; for a significant portion of the surgical field, preferably substantially all of it, a beam of light can be positioned in a desired region of the surgical field without need for moving the endoscope. In some variants of embodiments with a light beam smaller than the lens, the light beam can be moved relative to the lens and the lens can be moved relative to the endoscope, such that the angle at which the light enters the surgical field can be varied without need for movement of the endoscope.

In many cases, the endoscope cannot view the entire working space within the body, so the endoscope must be repositioned to allow the surgeon to view regions of interest within the space. However, moving the endoscope carries with it the danger of the endoscope contacting a tool and possibly moving it or, worse, contacting a portion of the body and possibly damaging it.

In many cases, the surgeon wants a close-up view of the working area; in other cases, an overview is desirable and a rapid transition from close-up to overview and vice-versa is also desirable.

The device disclosed herein uses an endoscopic camera in conjunction with a wide-angle lens and software for viewing control in order to provide an endoscopic system with digital maneuvering of the field of view, wherein both the center of the field of view (the position) and the extent of the field of view (the zoom) can be altered rapidly, in many cases, without need for physical movement of any part of the system. Furthermore, digital maneuvering can be either continuous or discrete.

The advantages of digital maneuvering (digital zoom and digital positioning) include:

There is very little or no need to physically alter the position of the endoscope in order to change the viewing angle, which can be especially important in robotic systems where robotic control of the viewing angle is used rather than human control.

Maneuvering of the endoscope is simplified—no moving parts are needed either for control of endoscope position or for control of components within the optical system.

Change in the viewing direction can be continuous, and discrete steps are not of fixed size, unlike the fixed-size discrete steps found in systems such as the Storz-EndoCameleon™.

In the Storz-EndoCameleon, manipulation of the field of view is carried out mechanically. FIG. 1 illustrates the discrete, although overlapping, fields of view (110) possible with the Storz-EndoCameleon of the prior art.

In the device disclosed herein, the use of a wide-angle lens allows primarily digital maneuvering of the endoscope. A wide-angle lens such as a fish-eye lens can provide an image of a large portion, if not all, of a working area, such as the interior of the abdomen. The image provided by a wide-angle lens is typically distorted; software can be used to correct the distortion.

A high resolution camera, preferably at least 4096×3072 pixels, can provide sufficient detail for digital maneuvering; 4D maneuvering including zoom can be implemented in software, minimizing the need to physically move the endoscope.

Two types of digital zoom are common in the art. In one, sometimes called "intelligent zoom" or "iZoom" and referred to herein as "interpolating zoom", for at least part of the zoom range, the camera has higher resolution (more pixels per unit area of the object(s) viewed) than the display, so that, as the inward digital zoom progresses and the display image enlarges, the display shows more resolution, as detail captured by the camera but not previously displayable becomes displayable.

The other common type of digital zoom will be referred to herein as "straight enlargement". In straight enlargement, for at least part of the zoom range, the camera has a resolution the same as or smaller than the resolution of the display, so that one camera image pixel will be mapped to one or more display pixels. It should be noted that "more than one display pixel" includes fractional numbers of pixels, where the fraction is greater than one. Straight enlargement can be carried out by any means known in the art, including, but not limited to, spreading the camera pixel over all the display pixels; averaging two or more camera pixels in cases where some fraction of each pixels maps, in part, to some fraction of a display pixel (none of the fractions need be the same), interpolating between camera pixels and any combination thereof.

In typical embodiments described herein, a member of a group consisting of interpolating zoom, straight enlargement and any combination thereof will be employed. Preferably, interpolating zoom will be employed.

Figure 2:
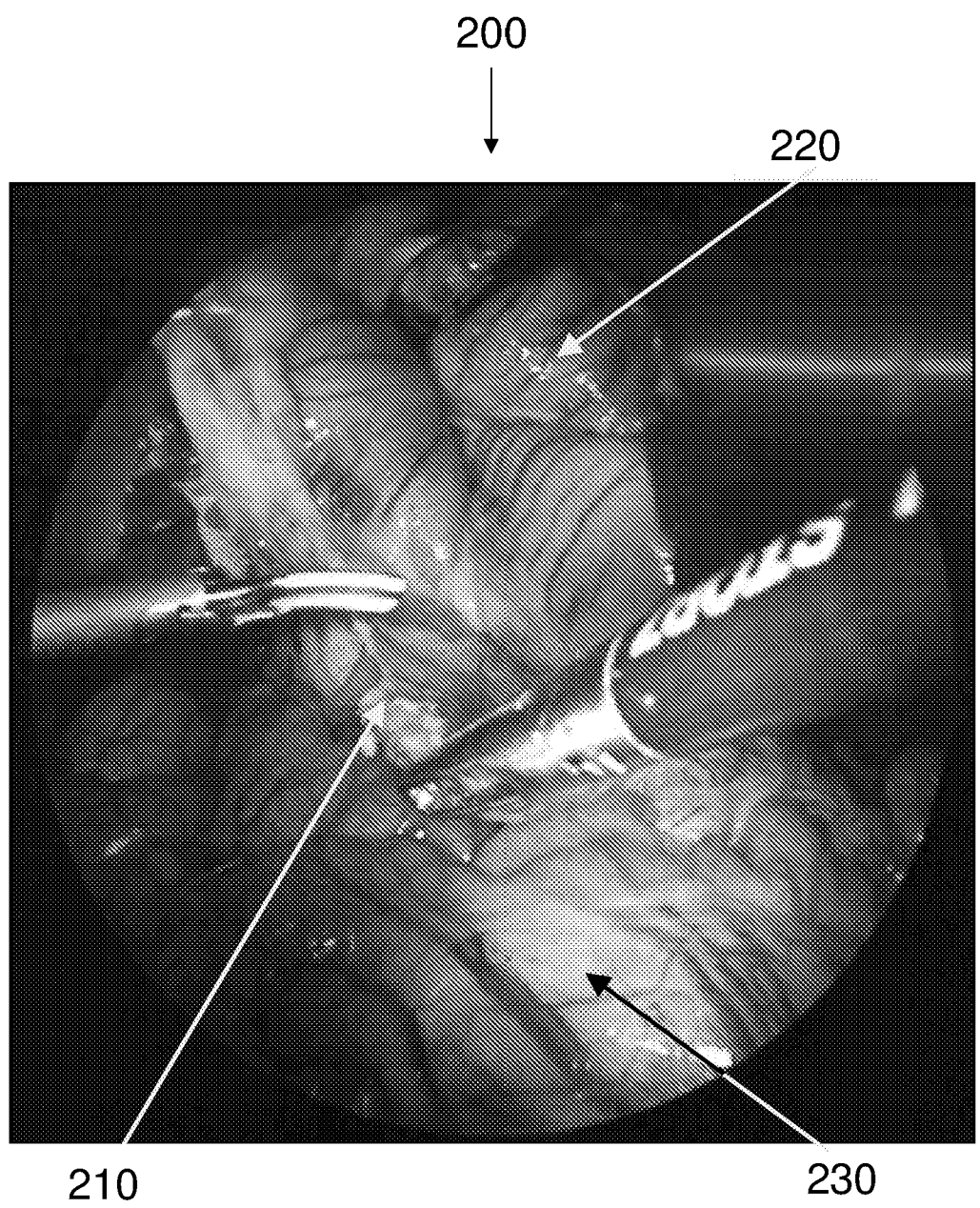
FIG. 2 depicts a high-resolution camera image of an operating field in the abdomen.

A typical image taken with a high-resolution camera is shown in FIG. 2; the image shows the detail provided by large number of pixels in the image from such a camera. It is the large number of pixels that enables zooming, since the image will remain clear and detailed even when a small portion of it is zoomed to fill the whole display. In FIG. 2, locations are shown for the centers of the enlarged images of FIG. 3 (210), FIG. 4 (220) and FIG. 5 (230).

Figure 3:
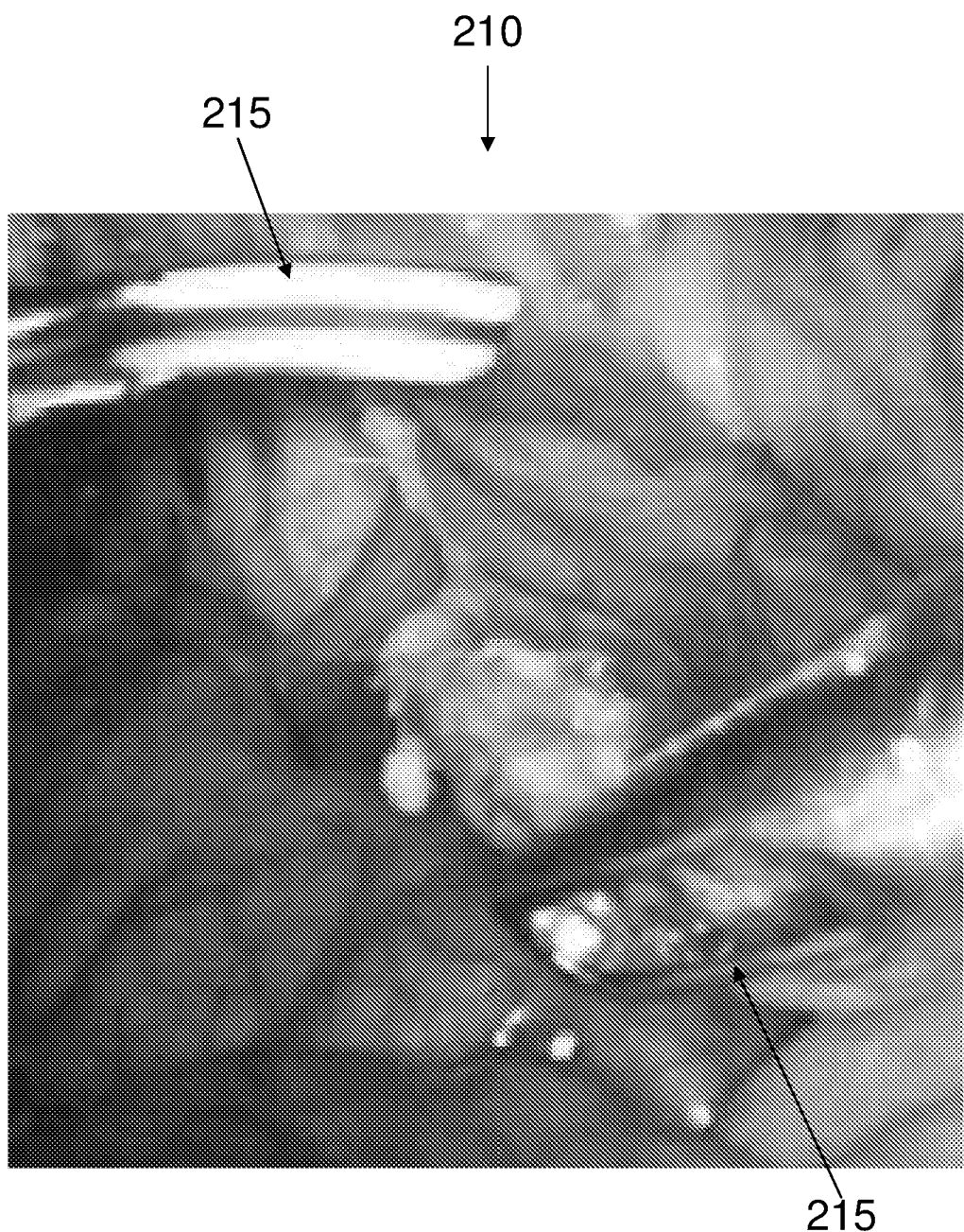
FIGS. 3-5 depict close-ups which are enlargements of portions of the image of FIG. 2.

FIG. 3 shows (210) an enlarged view of a portion of the image of FIG. 2, centered halfway between the tools. The enlarged image includes approximately 10% of the area of the original picture but details, such as the tools (215), remain clear. Again, said image is provided merely by image processing, not by physically maneuvering (or zooming) the endoscope.

Figure 4:
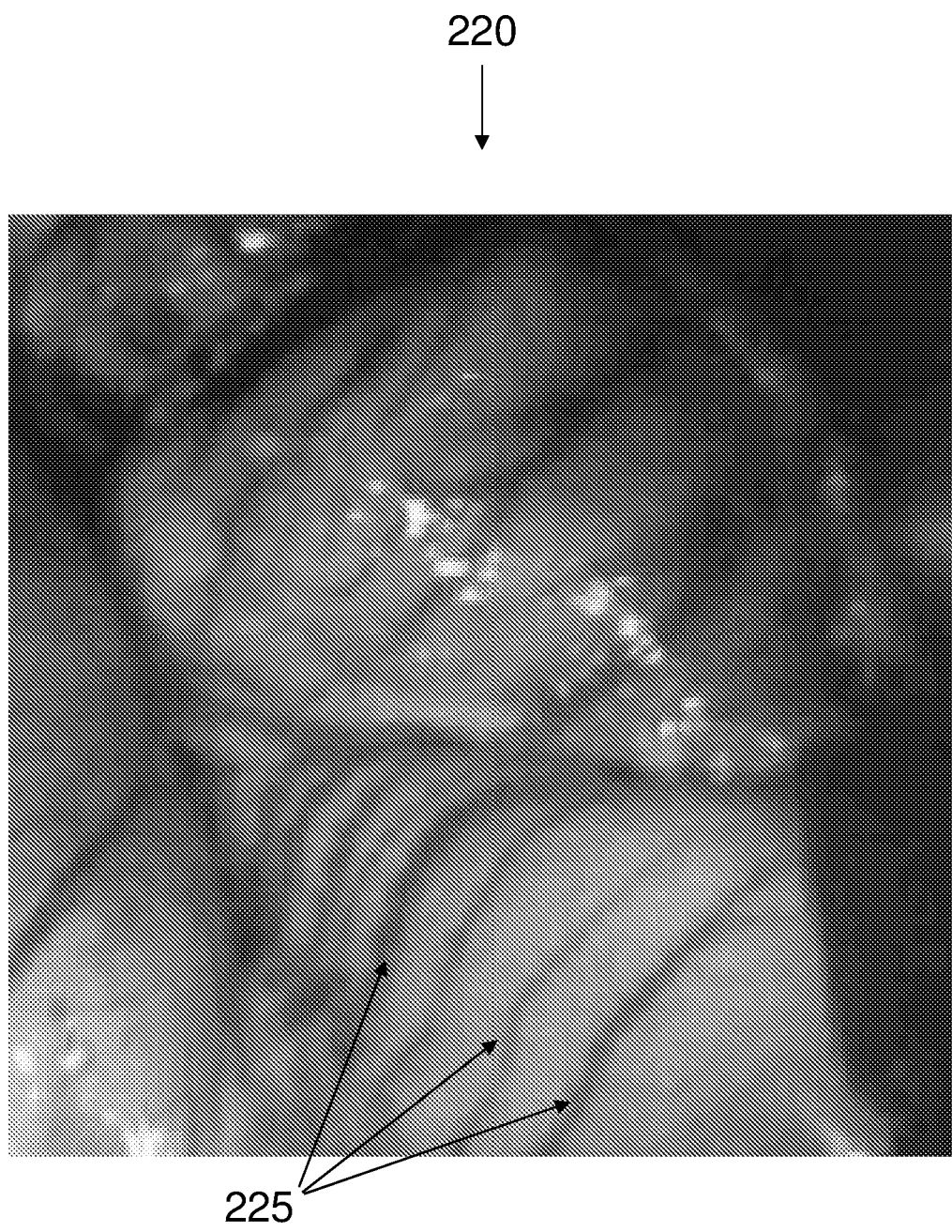

FIG. 4 shows (220) an enlarged view of a portion of the image of FIG. 2, centered on the lobe at the top right of the image of FIG. 2. The enlarged image includes approximately 10% of the area of the original picture but details, such as the blood vessels (225), remain clear. Again, said image is provided merely by image processing, not by physically maneuvering (or zooming) the endoscope.

Figure 5:
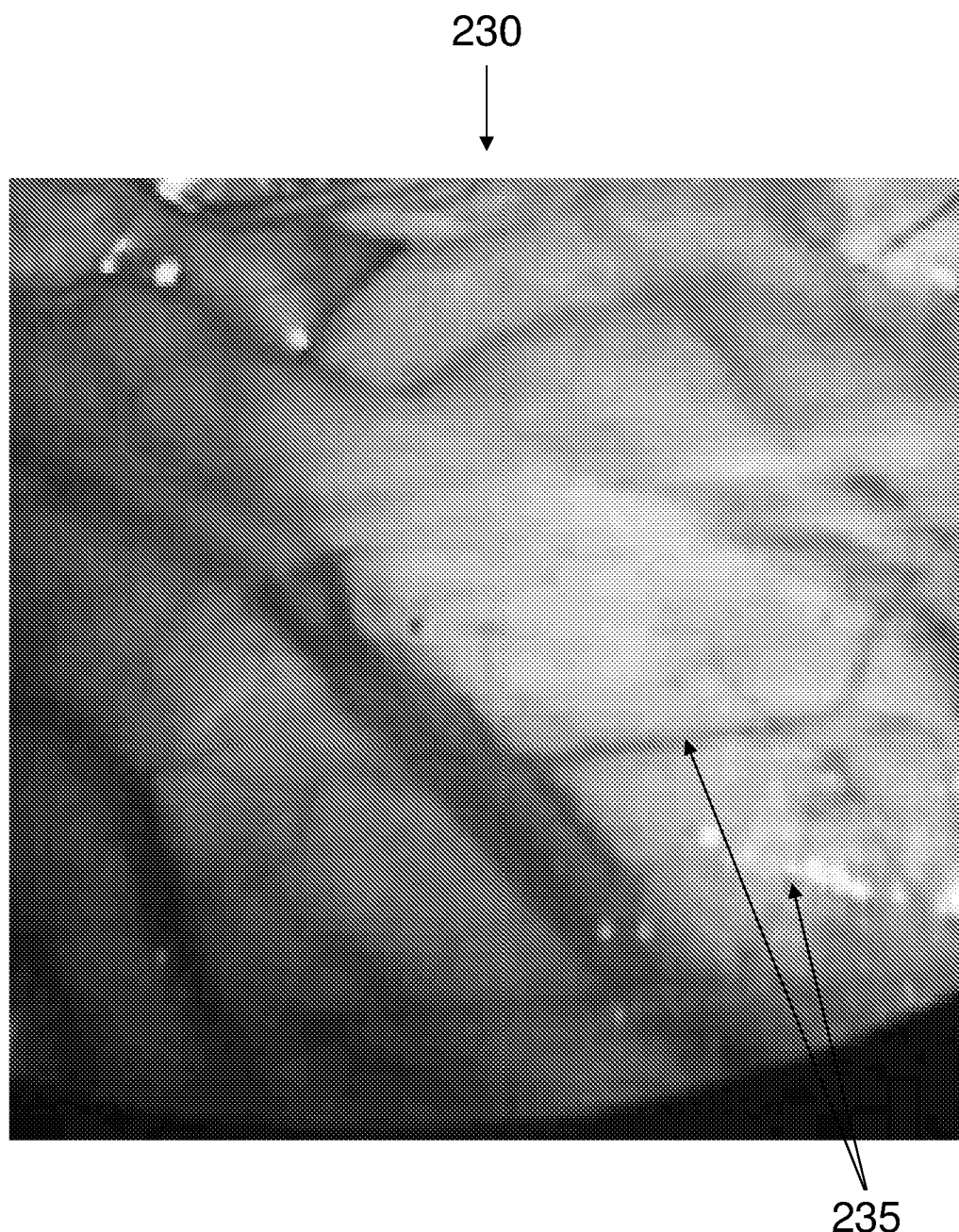

FIG. 5 shows (230) an enlarged view of a portion of the image of FIG. 2, centered on the lobe at the top right of the image of FIG. 2. The enlarged image includes approximately 10% of the area of the original picture, but details such as the blood vessels (235) remain clear. Again, said image is provided merely by image processing, not by physically maneuvering (or zooming) the endoscope.

In the device of the present invention, software is used to correct any distortion of the image caused by the lensing system, to digitally move the image to a display a selected portion of the field of view (position the image) and to digitally alter the size of the display view, the viewed portion of the field of view (zoom the image).

In many endoscopic systems, the tip lens in the camera optics is not at a right angle to the sides of the endoscope. Conventionally, the tip lens angle is described relative to a right angle, so that a tip lens at right angles to the sides of the endoscope is described as having an angle of 0. Typically, angled endoscope tip lenses have an angle of 30° or 45°. This tip lens angle affects the image seen during physical zooming. FIG. 6A-E illustrates, in an out-of-scale manner, for a conventional system, the effect of physical zooming in the field of view in an endoscope with tip lens set straight in the end (FIGS. 6A and 6C) vs. the effect of physical zooming in the field of view in an endoscope with angled tip lens (FIGS. 6D and 6E).

Figure 6A:
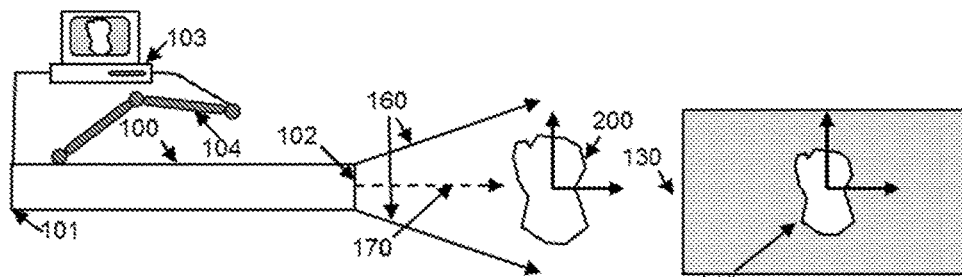
FIG. 6A-G illustrates the effect of tip angle on the center of the field of view or the direction of motion of a physically zoomed endoscope for endoscopes with differently angled tips.
Figure 6B:
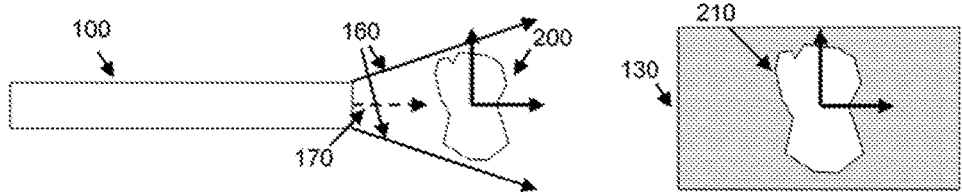
Figure 6C:
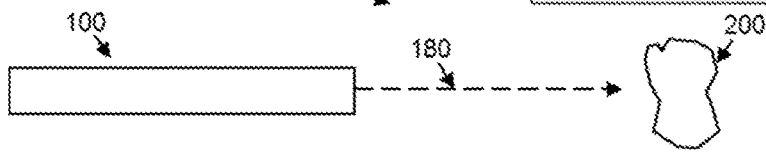
Figure 6D:
Figure 6E:
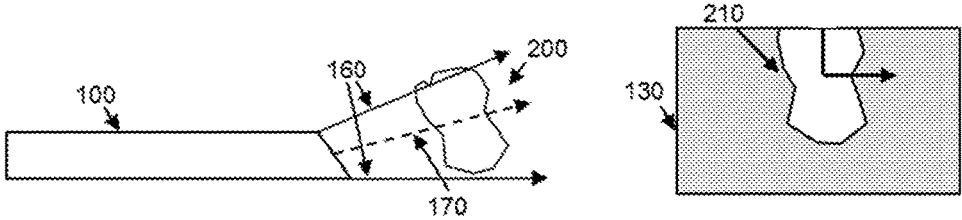

FIGS. 6A and 6E illustrate the endoscope (100), the object it is viewing (200) and the image seen by the endoscope camera (130) before the physical zoom. The solid arrows (160) show the limits of the field of view (FOV) and the dashed arrow (170), the center of the FOV; since the object is in the center of the FOV, an image of the object (210) is in the center of the camera image (130).

FIGS. 6B and 6E illustrate the endoscope (100), the object it is viewing (200) and the image seen by the endoscope camera (130) after the physical zoom. The solid arrows (160) show the limits of the FOV and the dashed arrow (170), the center of the field of view.

If the tip lens is set straight in the end of the endoscope (FIGS. 6A and 6B), an object (200) in the center FOV will be in the center of the FOV (and the camera image) (130) both before (FIG. 6A) and after (FIG. 6B) the physical zoom. As illustrated in an out-of-scale manner in FIG. 6C, the direction of motion of the endoscope during the physical zoom (180) is a straight line connecting the location of the center of the tip of the endoscope (100) at the start of the physical zoom with the center of the field of view at the start (and end) (170) of the physical zoom; the center of the endoscope tip will lie on this line at all times during the physical zoom.

However, if the tip lens is set at an angle in the end of the endoscope (FIGS. 6D and 6E), then an object that is in the center of the FOV (and the camera image) before the physical zoom (FIG. 6D) will not be in the center of the FOV (or the camera image) after the physical zoom (FIG. 6E) since the direction of motion of the endoscope is not the direction in which the center of the field of view (170) points.

Figure 6F:
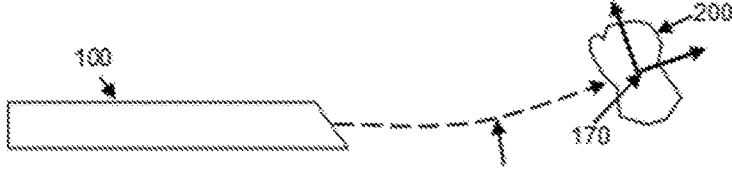
Figure 6G:
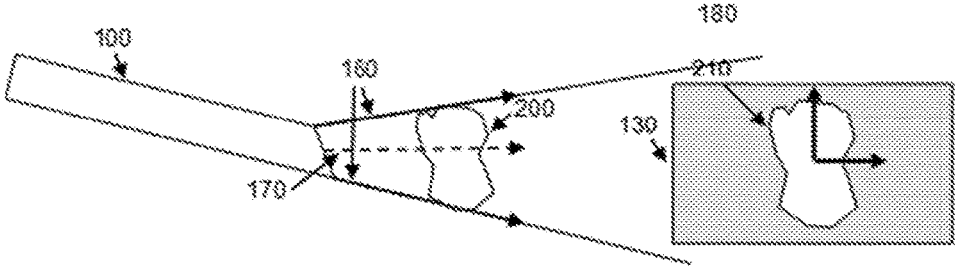

In some embodiments of the system of the present invention, the controlling means maintains a fixed center of the field of view (FOV) during physical zoom independent of the tip lens angle. In such systems, (FIGS. 6F and 6G) the endoscope (100) tip will move in a curved trajectory (180, FIG. 6F) such that the center of the FOV does not change during physical zooming (FIG. 6G).

Maintenance of a fixed center of the field of view can be can be made either by inputting the angle of the tip lens during setup, in which case, the system can calculate an appropriate trajectory, or by identifying the center of the field of view by analyzing the image. Inputting the tip lens angle means that no image analysis need be done; however, controlling the direction of motion of the endoscope during physical zoom via image analysis means that that the tip lens angle does not need to be input, obviating a possible source of error.

In preferred embodiments of the device of the present invention, both digital maneuvering and physical maneuvering are enabled so that maneuvering from one display view to another display view can include digital maneuvering, physical maneuvering, or both physical and digital maneuvering.

In preferred embodiments, the physical and digital movements comprising the maneuvering are under software control. A surgeon or other user directs the system to maneuver the display view; the software then controls the physical and digital movements needed to accomplish the desired maneuver. Physical maneuvering of the laparoscope or endoscope is accomplished by controlling the laparoscope's position and orientation. Combined digital and physical maneuvering can be used to achieve more flexibility in the viewed image, such as, for non-limiting example, inserted the laparoscope deeper into the operating region in order to view beyond an occluded organ, while digitally maneuvering display view in order to tilt the viewing angle.

Digital maneuvering of the display view can also be performed automatically by an algorithm in order to achieve a predefined goal such as (but not limited to) centering a certain object in the image, zooming in or out in order to maintain a certain object size, rotating the image in order to maintain a constant horizon and any combination thereof. For non-limiting example, a surgeon can instruct the system to retain a specified tool in the center of the display image. If the surgeon moves the tool towards himself (and away from the operating site) and to the right, the display view will automatically zoom outward (shrinking the apparent size of the operating site) and will track to the right (moving the operating site to the left in the display view).

The surgeon can control maneuvering in an accustomed manner, by moving a moving element, whether the movement of the moving element be by moving an object, by touching a prepared surface, by typing on a keyboard, by a gesture, by a non-gesture body movement, by a sound signal, by an electrical or magnetic signal indicating movement of at least one muscle, by an encephalographic pattern indicating movement of at least one muscle, by an encephalographic pattern indicating future movement of at least one muscle, and any combination thereof.

For non-limiting example, the moved object can be a joystick, a lever, a button or a slider.

For non-limiting example, the prepared surface can be a touch-sensitive pad with commands on it, or the display can comprise a touchscreen and the surgeon can touch the location in the image which will form the center of the field of view, and can zoom by drawing the outline of the desired image area on the display, or by holding his finger on the screen until zoom is completed. Any combination of the above can also be used.

For non-limiting example, a gesture can comprise a hand movement, an arm movement, a body movement, a head movement, an eye movement, and any combination thereof.

For non-limiting example, the sound can comprise a word, a predetermined sound pattern such as a sound of predetermined pitch, either constant or varying, a sound of constant loudness, a sound of varying loudness and any combination thereof.

In some embodiments, control of the tools and of maneuvering of the laparoscope does not require physical contact between the surgeon and either the tools or the laparoscope. Control of at least one tool and/or maneuvering of an endoscope can be via at least one predetermined input command associated with a predetermined output command or predetermined output protocol, or via detection, by the system, of an input procedure, with the output procedure dependent on at least one of the input procedure and other information accessible to the system.

The system of the present invention can be used in a conventional manner, with the operator and other members of the operating team in the same room as the patient during the operation, or the system of the present invention can be used for remote surgery, with the operator controlling the laparoscope and the tools from a location remote from the patient. In addition, control of maneuvering of a tool or the laparoscope can be done without a joystick or other object which requires the operator, during the operation, to place his hand in contact with the device.

In some embodiments, the system provides an override facility such that an undesired movement can be overridden. The override can be a voice command, a movement, an intended movement or a thought. The movement or intended movement can be movement of a hand, an eye, an arm, a finger, a chest, a neck, a head, a mouth, a tongue, vocal cords (a predetermined sound), a leg, a toe, a foot or any combination thereof. An actual movement can be detected by any movement detection means, as described hereinbelow. An intended movement can be detected by means of muscular electric or magnetic patterns, as described hereinbelow, or from encephalographic patterns ("brain waves"), as described hereinbelow. Similarly an override thought can be detected by means of encephalographic patterns.

In some embodiments, the system can identify at least one unwanted movement protocol for at least one moving element. Non-limiting examples of unwanted movement protocols include: involuntary movement of a body part, saccadic movement of an eye, vestibulo-ocular movement of an eye, winking an eye, blinking an eye, tremor of a body part, a tic in a body part, myoclonus of a body part, dystonia, and any combination thereof.

In such embodiments, the preferred response is for the system to ignore the unwanted movement, so that the actual output movement is unaffected by and substantially independent of the unwanted movement. For non-limiting example, in a system where the movement of an endoscope is proportional to movement of an eye, the jerkiness of the actual eye movement, imparted both by saccadic movement and vestibule-ocular movement, will be "programmed out" so that the movement of the endoscope is smooth. Similarly, if eye movement is controlling movement of an endoscope to the right, a quick glance upward will be "programmed out"; the endoscope will not diverge from the direct path to the right.

In another non-limiting example, movement of two retractors is controlled by movement of two arms. During a retraction to further open an incision, the operator suffers a muscular twitch that jerks an arm upward. The jerk is ignored so that the retractors move apart smoothly.

For non-limiting example, if the surgeon commands a movement of the center of the field of view in a given direction, the surgeon will see the center of the field of view moving in that direction, although neither the endoscope nor the camera nor the lenses nor any of the camera optics will have physically moved. Similarly, a command to zoom in on the center of the field of view will cause the image to zoom, enlarging the image of the center of the field of view while reducing the portion of the image which is shown. Again, there will have been no physical movement of the endoscope, of any lens, of the camera, or of any component of the camera optics.

In preferred embodiments, discrete alteration of the field of view is also enabled. Again, although there is digital movement—the image on the display changes—no physical movement is involved; there was no physical movement of the endoscope, the camera, the lenses or any part of the camera optics.

In embodiments with discrete alteration of the field of view, for non-limiting example, a user may wish to have an overview of the situation, by switching from a close-up of the area on which he is working to view of a large portion of the interior of the abdomen. This can be desirable, for non-limiting example, if the surgeon suspects that there may be bleeding and wishes to find the source of the bleeding in order to stop it.

In some variants of embodiments with discrete alteration of the field of view, switching is from (and back to) the current position and zoom, with switching to (and from) a single, predetermined, overview position, with a single, predetermined zoom and position. Preferably, this single, predetermined zoom and position includes in the image digitally all of a working area such as, but not limited to, the interior of the abdomen.

In other variants of embodiments with discrete alteration of the field of view, the surgeon can select desired overview positions and zooms, selected overview positions and zooms being stored in a database. As a non-limiting example, at the beginning of an operation, the surgeon can examine the image and create overviews by selecting desired positions, and, for each desired position, adjusting the zoom, then storing the resulting position and zoom in the database. During the operation, when a desired overview is selected, the image "jumps" so as to display an image with that overview's position and zoom. The surgeon can then either jump back to the previous close-up view, or jump to another overview.

In some embodiment, the system comprises predetermined locations on the display, such that, by positioning a movable article such as, but not limited to, a tool within the predetermined location, the system performs a predetermined action. The predetermined location can be the location on the display of an article, or it can be an icon or popup. Icons are preferably at the edges of the display, although they can be anywhere on the display or even in a separate display; popups can occur anywhere, including at the edge of the display, elsewhere on the display, or on a separate display.

For non-limiting examples:
- In some embodiments, at least one full-screen location is provided, which commands a switch between any view and an overview encompassing the entire field of view of the image.
- In some embodiments, at least one "return to previous view" location is provided, which commands a switch back to at least one previous zoom and center.
- In some embodiments, a single location switches between full-screen mode and return-to-previous mode.
- In some embodiments, the return-to-previous location can return to a plurality of previous views. For non-limiting example, each time the movable article enters the return-to-previous location, the view switches back another view.
- In some embodiments, there is at least one go-to-next location, which commands a switch forward to at least one subsequent zoom and center.
- In some embodiments, there is at least one switch-between location, which enables switching, as described above, between predetermined overview positions and zooms.
- In some embodiments, there is at least one warning location, such that, as described hereinbelow, an operator can be warned of an item of interest occurring outside of the displayed region.
- In some embodiments, there is at least one go-to location, such that, as described hereinbelow, the region where the item of interest is occurring can be displayed, either by enlarging the field of view or by switching the center of the field of view to the region where the item of interest is occurring.

Figure 7A:
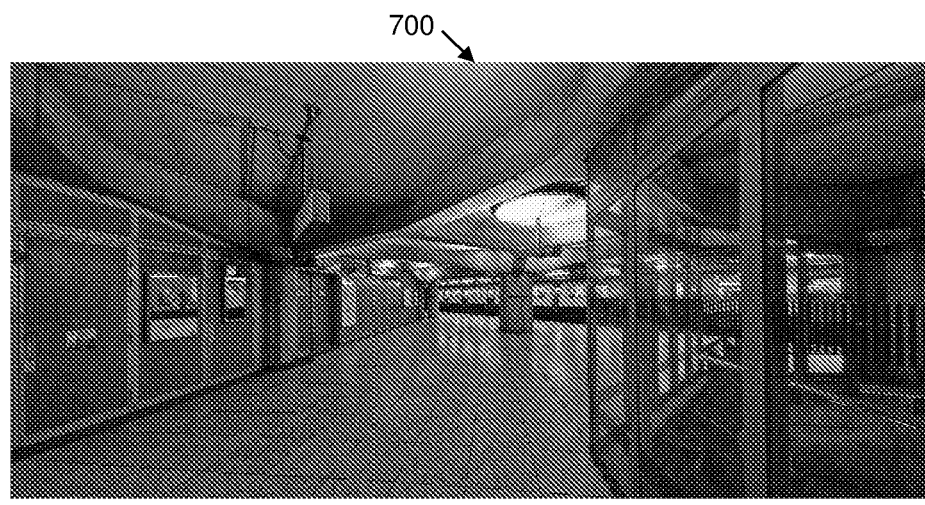
FIG. 7A-B illustrates a scene, both as it appears and as captured by a camera viewing it through a fisheye lens.
Figure 7B:
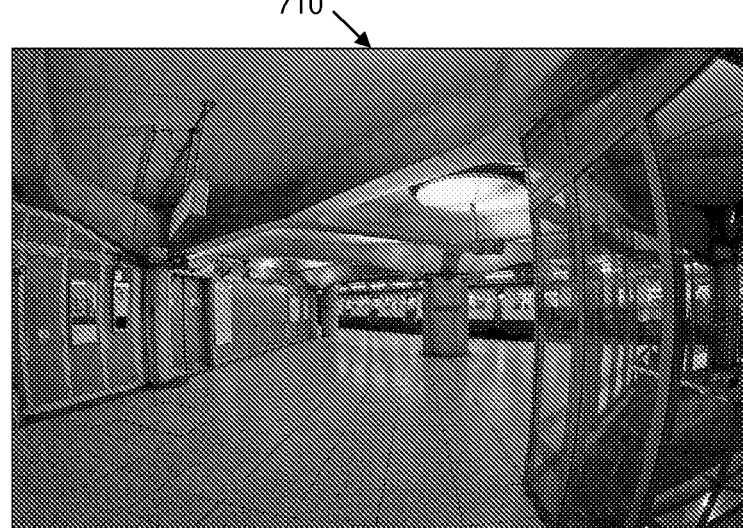

In most embodiments of the system, the region viewed by the lens is significantly larger than the region displayed. FIG. 7A shows a non-limiting example of a region (700) viewable by a fisheye lens, in this case a railway station, while FIG. 7B shows the whole of the image as captured by a camera using the fisheye lens (710).

Figure 8A:
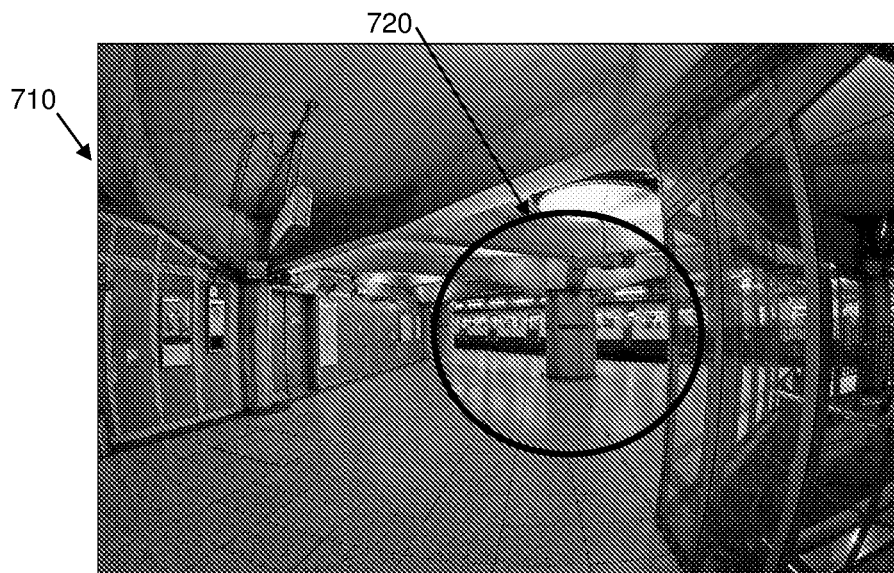
FIG. 8A-B illustrates a scene as captured by a camera and a field of view as displayed.
Figure 8B:
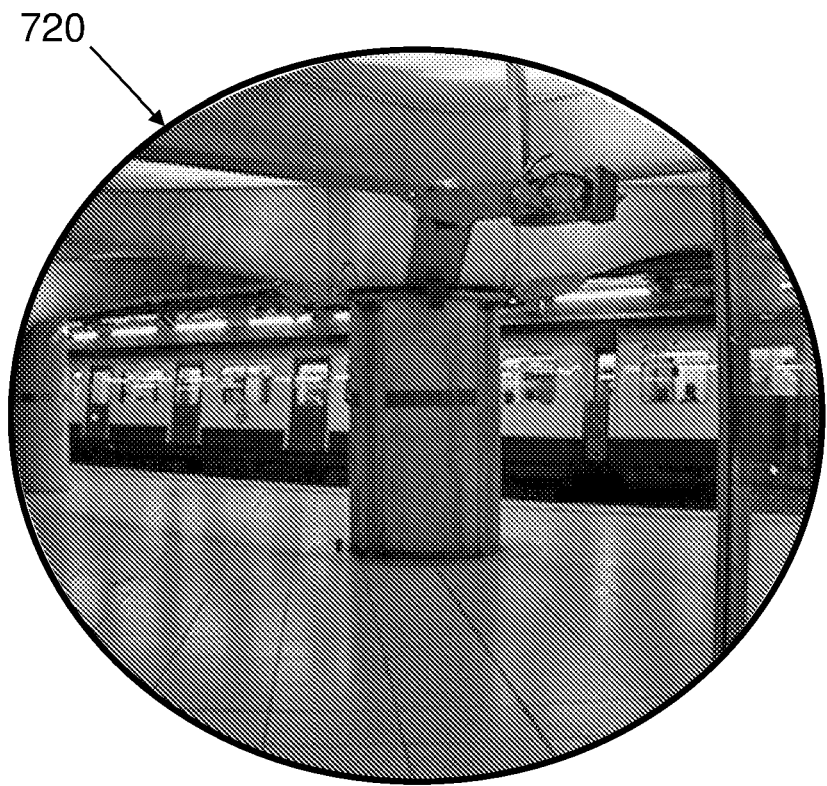

FIG. 8A shows, on the fisheye lens image (710) the limits of the field of view of a display (720), while FIG. 8B shows the image as seen in the display (720), with the distortions of the fisheye lens removed by software.

In some embodiments of the system, image analysis is done so that the system "knows" what is happening outside the displayed image, but within the field of view of the lens. In such embodiments, the operator can be provided with a warning if something of interest has occurred outside the field of view of the display, but within the field of view of the lens.

Items of interest can include, but are not limited to, an article entering the field of view of the lens, an article moving, a likely collision between two articles, the occurrence of bleeding, the edges of an incision moving, activation or deactivation of a tool, articulation of a tool, and any combination thereof.

Non-limiting examples of collisions between two articles are: a collision between two or more tools, and a collision between at least one tool and an organ.

The warning can be visual or aural, with an aural warning selected from a group consisting of a predetermined voice message or a predetermined sound. A visual warning can be selected from a group consisting of a light, either flashing or steady, or a region on the display changing in quality, where the change in quality can include, but is not limited to, changing color, changing brightness, a pop-up appearing, an icon or other symbol ungreying, and any combination thereof.

Figure 9A:
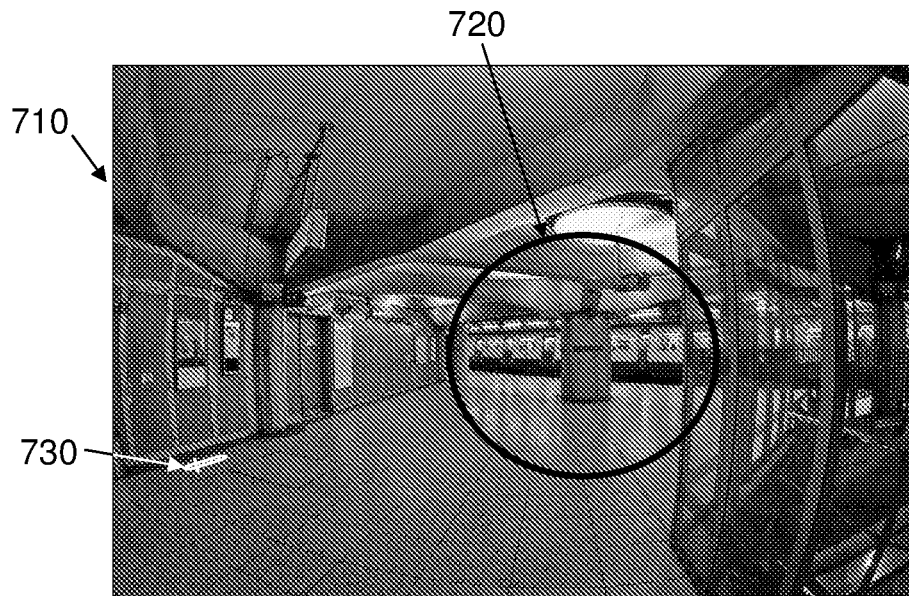
FIG. 9A-D illustrates a scene which includes an item of interest as captured by a camera, a display field of view showing a popup, a display field of view showing a warning and a display field of view which encompasses the item of interest.

FIG. 9A shows the scene of FIG. 7A, with the addition of an exemplary item of interest, a sword.

Figure 9B:
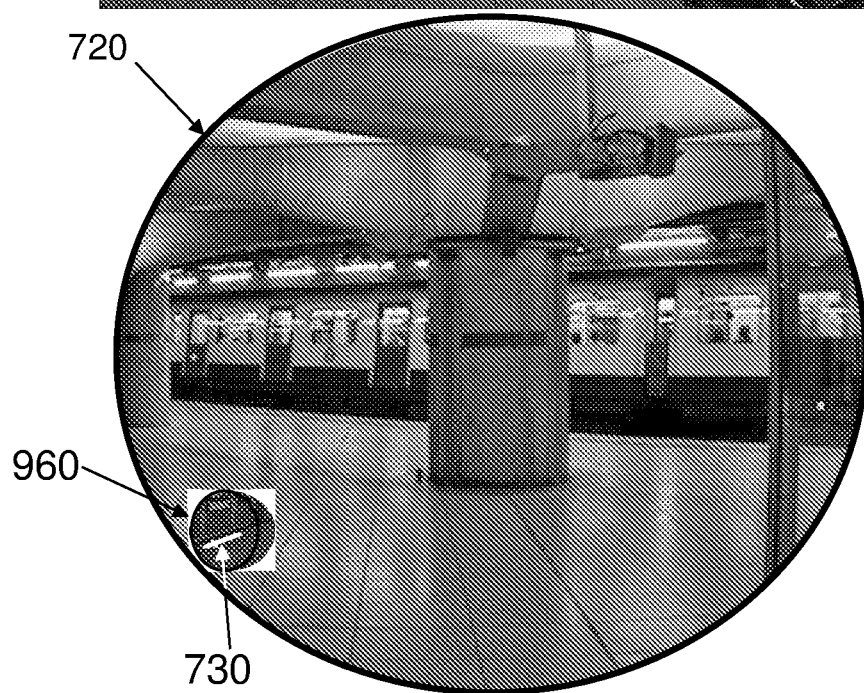

FIG. 9B shows visual warning, a popup (950), indicating the existence of the item of interest (730) outside the field of view of the display (720). In this embodiment, the location of the popup indicates that the item of interest is in the lower left quadrant of the field of view of the fisheye lens (710). A popup can be in a fixed position, it can use an arrow or other directional symbol to indicate the direction of the item of interest with respect to the icon or with respect to a fixed position (such as the center of the field of view), it can use different weight or different color symbols to indicate a distance to the item of interest, or a text message indicating direction, distance or both. The text message can be on the warning, or it can form part of a separate warning, which can be any type of visual or aural message as described hereinabove for a warning. Any combination of the above warnings and/or direction indicators and/or distance indicators can be used.

The system can provide preferred responses by means of which an operator can respond quickly to the warning. Such preferred responses can include, but are not limited to, moving the center of the field of view to the region where the item of interest is occurring, with or without zooming to improve the view of the region; zooming outward so that the field of view includes both the original field of view and the region where the item of interest is occurring, and any combination thereof.

A preferred response can be selected by positioning a movable article, preferably a tool, in a predetermined region of the display, such as on an icon or popup; by a predetermined movement of a movable article, preferably a tool; by touching a predetermined location on a screen, such as an icon or popup and any combination thereof.

Figure 9C:
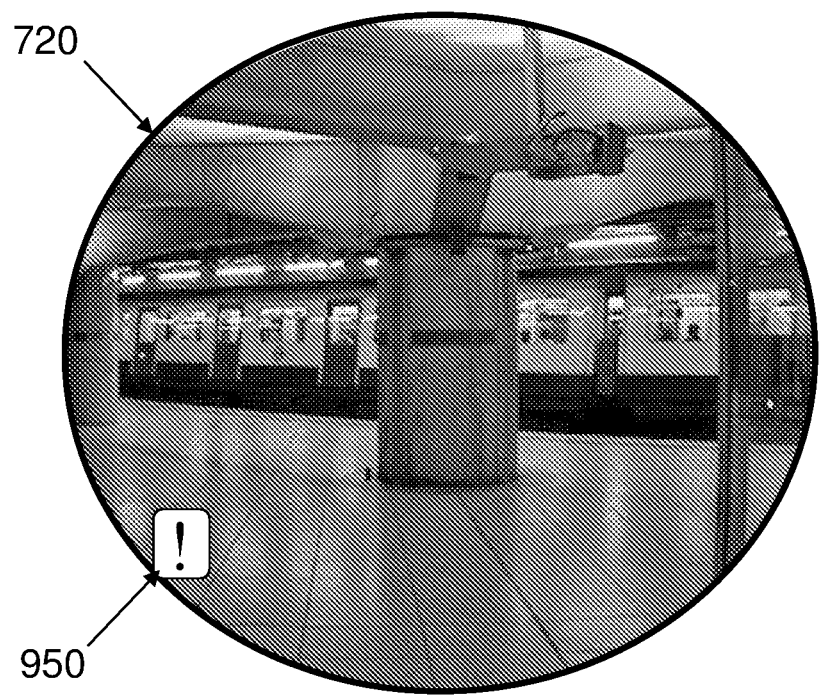
Figure 9D:
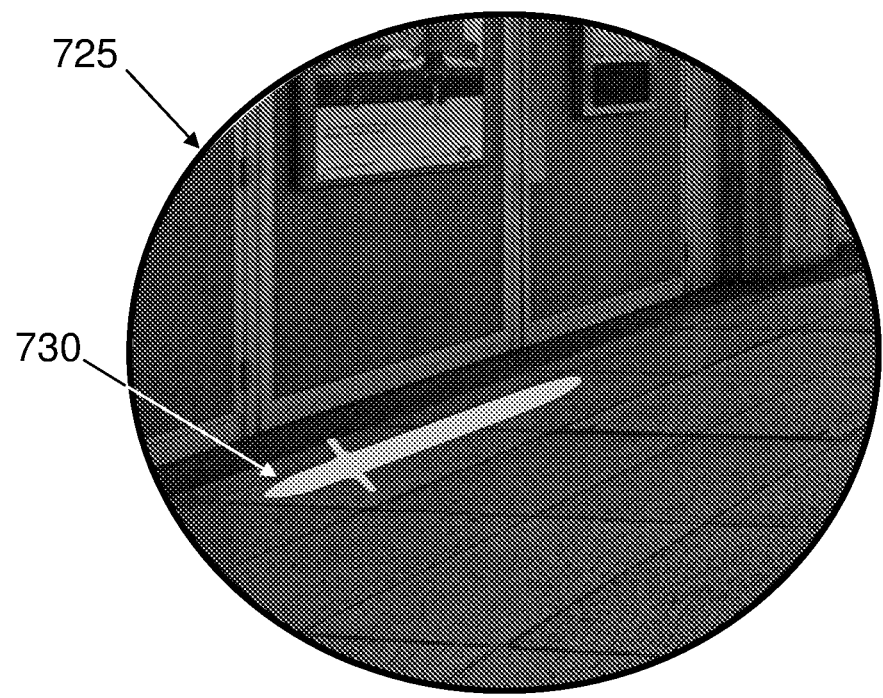

FIG. 9C shows a field of view of the display (725) which includes the item of interest, as it would appear in some embodiments of the system. In this example, the magnification is the same for the original field of view and the field of view including the sword. In other embodiments, other magnifications can be used.

In the embodiment shown, the field of view of the display (725) showing the item of interest entirely replaces the previous field of view of the display (720). In other embodiments, a display field of view which includes the item of interest can appear as a popup or can replace only a portion of the earlier display field of view as in, for non limiting example, a split screen.

It should also be noted how distorted the camera image is at the location of the item of interest, the sword, since the sword is near the edge of the field of view of the fisheye lens and of the camera.

it should be noted that software manipulation of the size and location of the display field of view, and software manipulation of the size and location of the illuminated region minimize the need for hardware manipulation, thereby minimizing the size and complexity of manipulation hardware and maximizing the space within the endoscope and/or the surgical field which is available for other purposes.

It should further be noted that in embodiments with automatic control of the size and location of the display field of view, no human assistant is needed to manipulate the field of view, thereby eliminating a source of human error.

It should also be noted that in embodiments with automatic control of the size and location of the illuminated region, no human assistant is needed to manipulate the field of view, thereby eliminating a source of human error.

The invention claimed is:

1. A method of alerting a user to events during surgery, comprising:
    positioning an endoscope having a field of view in a body cavity, and capturing images of the body cavity using an endoscope;
    selecting a portion of said field of view and displaying said portion of the field of view on the display;
    providing a popup image upon image analysis identification of an occurrence of bleeding within the field of view but outside the portion of said field of view, said popup image comprising at least one overlay on the portion of the field of view displayed on the display, wherein said overlay comprises an image of an area of said occurrence of bleeding and is positioned to indicate a location of the bleeding relative to the portion of the field of view.

2. The method of claim 1, wherein the method additionally comprises controlling at least one aspect of illumination of said field of view when displayed on the display.

3. The method to claim 1, wherein the method additionally comprises automatically digitally moving said images to display a selected at least a portion of said field of view to maintain a predetermined object at the center of said portion of said field of view.

4. The method of claim 1, wherein the method additionally comprises automatically digitally moving said images to display a selected at least a portion of said field of view to maintain a predetermined horizon.

5. The method of claim 1, wherein the method additionally comprises automatically digitally moving said images to display a selected at least a portion of said field of view to maintain a predetermined object at a predetermined apparent size.

6. The method of claim 1, wherein the method additionally comprises automatically selecting a portion of a field of view; removing distortion from said portion of the field of view, and displaying said portion of said field of view on the display.

7. The method of claim 1, wherein the method additionally comprises combining said images to form a display image, said display image selected from a group consisting of: a unitary two-dimensional display; a unitary three-dimensional display; a stereoscopic display and any combination thereof.

8. A method of alerting a user to events during surgery, comprising:
    positioning an endoscope having a field of view in a body cavity, and capturing images of the body cavity using an endoscope;
    selecting a portion of said field of view and displaying said portion of the field of view on the display;
    providing a popup image upon image analysis identification of an occurrence of motion of edges of an incision within the field of view but outside the portion of said field of view, said popup image comprising at least one overlay on the portion of the field of view displayed on the display, wherein said overlay comprises an image of an area of said occurrence of motion of edges of an incision and is positioned to indicate a location of the motion of edges of an incision relative to the portion of the field of view.

9. The method of claim 8, wherein the method additionally comprises controlling at least one aspect of illumination of said field of view when displayed on the display.

10. The method to claim 8, wherein the method additionally comprises automatically digitally moving said images to display a selected at least a portion of said field of view to maintain a predetermined object at the center of said portion of said field of view.

11. The method of claim 8, wherein the method additionally comprises automatically digitally moving said images to display a selected at least a portion of said field of view to maintain a predetermined horizon.

12. The method of claim 8, wherein the method additionally comprises automatically digitally moving said images to display a selected at least a portion of said field of view to maintain a predetermined object at a predetermined apparent size.

13. The method of claim 8, wherein the method additionally comprises automatically selecting a portion of a field of view; removing distortion from said portion of the field of view, and displaying said portion of said field of view on the display.

14. The method of claim 8, wherein the method additionally comprises combining said images to form a display image, said display image selected from a group consisting of: a unitary two-dimensional display; a unitary three-dimensional display; a stereoscopic display and any combination thereof.

* * * * *